United States Patent [19]
Chubachi

[11] Patent Number: 4,655,083
[45] Date of Patent: Apr. 7, 1987

[54] SURFACE ULTRASONIC WAVE INTERFERENCE MICROSCOPE

[76] Inventor: Noriyoshi Chubachi, 4-6-203, Katahira 1-chome, Sendai-shi, Miyagi 980, Japan

[21] Appl. No.: 845,272
[22] PCT Filed: Jul. 8, 1985
[86] PCT No.: PCT/JP85/00384
   § 371 Date: Mar. 4, 1986
   § 102(e) Date: Mar. 4, 1986
[87] PCT Pub. No.: WO86/00710
   PCT Pub. Date: Jan. 30, 1986

[30] Foreign Application Priority Data
   Jul. 8, 1984 [JP] Japan ................... 59-141204
   Mar. 13, 1985 [JP] Japan ................... 60-51190

[51] Int. Cl.⁴ ............................................. G01N 29/00
[52] U.S. Cl. ........................... 73/606; 73/627; 73/633
[58] Field of Search ............... 73/606, 607, 627, 628, 73/633

[56] References Cited
U.S. PATENT DOCUMENTS
4,459,852  7/1984  Chubachi et al. ............ 73/606
4,503,708  3/1985  Kino et al. .................. 73/606
4,541,281  9/1985  Chubachi .................... 73/606

*Primary Examiner*—Howard A. Birmiel
*Attorney, Agent, or Firm*—Pollock, Vande Sande and Priddy

[57] ABSTRACT

A transmitting ultrasonic transducer (20) is excited by high-frequency pulses from a high-frequency pulse generator (1), a leaky elastic surface wave is excited in a sample (6) by a focused ultrasonic beam from the transducer (20), a reradiated wave of the leaky elastic surface wave is received by a receiving ultrasonic transducer (24), the received signal is applied to a mixer (23), wherein the phase difference between the received signal and a reference signal from a high-frequency oscillator (18) in the high-frequency pulse generator (1) is detected, and the detected output is provided as a display signal to a display (9 or 14). The transducers (20) and (24) and the sample (6) are moved by a drive means (7 or 10) relative to each other two-dimensionally in a plane parallel to the sample surface or in a direction perpendicular to the sample surface, and in synchronism with the movement, the display screen of the display (9 or 14) is swept, displaying thereon an ultrasonic microscopic image or a V(z) curve.

26 Claims, 27 Drawing Figures

SURFACE ULTRASONIC WAVE INTERFERENCE MICROSCOPE

TECHNICAL FIELD

The present invention relates to a surface ultrasonic wave interference microscope which excites leaky elastic surface waves on the surface of a sample and detects their reradiated waves, thereby measuring elastic properties of the sample qualitatively and quantitatively.

BACKGROUND ART

In recent years, there has been developed a mechanically scanning ultrasonic microscope for observing and measuring microscopic structural and acoustic characteristics of a material through use of a focused ultrasonic beam. This ultrasonic microscope, in principle, applies a conically focused ultrasonic beam to a sample, shifts the focal point of the ultrasonic beam in the plane of the sample, or in a direction perpendicular thereto, detects, by means of an ultrasonic transducer, reflected or transmitted ultrasonic waves resulting from different elastic properties of the sample at different points therein and converts them into electric signals for a two-dimensional display on a CRT screen to obtain an ultrasonic microscopic image, or for recording into an X-Y recorder or the like. Typical transducers for producing the focused ultrasonic beam are of the lens system and of the type in which an ultrasonic transducer is disposed on a concave or convex spherical surface. Furthermore, ultrasonic microscopes are divided into the transmission type and the reflection type according to the location of the ultrasonic transducer (for example, "Acoustic Microscopy with Mechanical Scanning—A Review", Proceeding of the IEEE, Vol. 67, No. 8, August 1979, pp. 1092-1113).

FIG. 1 is a block diagram illustrating the conventional reflection type ultrasonic microscope, which employs an acoustic lens for creating a focused ultrasonic beam and in which high-frequency pulses (a so-called burstlike signal) from a high-frequency pulse generator 1, which are obtained through ON-OFF modulation of a carrier with pulses, are applied via a directional coupler 2 to a focusing ultrasonic transducer 3, wherein they are converted into a conically focused ultrasonic beam 17, which is directed via a liquid acoustic field medium 4 to a sample 6 fixed to a holder 5. The sample 6 is disposed in the vicinity of the focal point of the ultrasonic beam. The holder 5 is moved by an XY-direction driver 7 in two perpendicularly intersecting X- and Y-directions which are perpendicular to the center axis of the ultrasonic beam 17. It is also possible, of course, to move the focusing ultrasonic transducer 3 in the X- and Y-directions instead of moving the holder 5. The XY-direction driver 7 is controlled by a scanning control signal from a scanning control circuit 8. Reflected waves from the sample 6 are collected or received by the focusing ultrasonic transducer 3, wherein they are converted into electric signals, and the received signals are provided via the directional coupler 2 to a display 9, the display screen of which is scanned two-dimensionally by the scanning control signal from the scanning control circuit 8, providing an ultrasonic microscopic image on the screen.

For the mechanism that produces contrast in the microscopic image obtainable with the conventional reflection type ultrasonic microscope, the relation between the focal point of the acoustic lens and the position of the sample is of importance, and this is explained as follows: FIG. 2 is a diagram for explaining it. In FIG. 2, the surface 6a of the sample 6 which is to be observed is slightly deviated from the position of the focal point $F_p$ of the ultrasonic beam toward an acoustic lens 11. Among incident waves of the ultrasonic beam 17 which are radiated from the acoustic lens 11 of a wide angular aperture, those incident waves which lie within a critical angle $\theta c$, which is dependent upon the sound velocity ratio between the liquid sound field medium 4 and the sample 6, are reflected in the same phase. Among such incident waves, a vertical incident wave which is incident to the sample surface 6a vertically thereto is reflected back to a transducer element 16, such as a piezoelectric film, via a route indicated by 10 (This incident wave will hereinafter be referred to as the vertical reflected wave). On the other hand, ultrasonic waves incident to the sample surface 6a in the vicinity of the critical angle $\theta c$ excite leaky elastic surface waves in the sample surface. The leaky elastic surface waves propagate in the sample surface 6a while reradiating ultrasonic waves to the liquid sound field medium 4. Of the reradiated waves (hereinafter referred to as the leaky radiated waves) by the leaky elastic surface waves, only a reradiated wave from a specific position on the sample surface 6a is reflected back to the transducer element 16 via a route indicated by 12. Accordingly, when the waves reflected back to the transducer element 16 via the routes 10 and 12 are superimposed upon each other, interference is caused and the output of the transducer element goes high or low depending upon whether the both waves are in phase with each other or 180° out of phase.

The critical angle $\theta c$ is determined by the Snell's law according to the ratio between the velocity of sound in the liquid sound field medium 4 and the velocity of a transverse wave in the sample 6. Since the velocity of sound in the sample 6 depends upon its density and modulus of elasticity, if the density and modulus of elasticity of the sample 6 vary according to the position therein, the critical angle $\theta c$ also varies accordingly. That is, when the sample surface 6a is scanned by the ultrasonic beam, the phase relationship between the ultrasonic waves travelling along the paths 10 and 12 undergoes changes in accordance with variations in the abovesaid density and modulus of elasticity. In consequence, the intensity of an interference signal resulting from the superimposition of the waves travelling along the paths 10 and 12 markedly changes at each point on the sample surface 6a, producing contrast in the image displayed on the display 9.

This conventional ultrasonic microscope uses a conically focused ultrasonic beam. Because of the symmetrical configuration of the focused ultrasonic beam, its component spreads in all directions around the beam axis. On this account, even if the sample has anisotropy about the Z-axis (perpendicular to the sample surface 6a), it is imaged as what is called averaged information which is independent of the direction of wave propagation.

On the other hand, there has been developed an ultrasonic microscope which measures the velocity of sound in a microscopic part of the sample surface without two-dimensional scanning of the sample by the ultrasonic beam, in addition to the ultrasonic microscope which obtains such a two-dimensional image as described above. FIG. 3 illustrates the arrangement of this conventional ultrasonic microscope which performs the abovesaid measurement of the velocity of sound. In FIG. 3, the same reference numerals as those in FIG. 1 indicate the same parts. The same is true of the other drawings. In FIG. 3, the sample 6 (a solid material, for instance) placed on the holder 5 is observed by monitoring the output of the focusing ultrasonic transducer 3 on an oscilloscope 14 while moving the sample holder by a Z-direction driver 13 toward the ultrasonic transducer 3. The display screen of the oscilloscope 14 is swept in the lateral direction (in the X direction) in synchronism with the movement of the sample by the Z direction driver 13. By recording the output of the focusing ultrasonic transducer 3 relative to the distance of movement of the sample in the Z-direction, such a curve as shown in FIG. 4 is obtained. This curve is called a V(z) curve or acoustic characteristic curve.

The reason for which such a curve can be obtained is the same as that described previously with regard to FIG. 2. That is, this phenomenon results from the interference between the reflected wave of the focused ultrasonic beam along the Z-axis (the vertical reflected wave travelling along the path 10) and the reradiated wave of the leaky elastic surface wave (the leaky reradiated wave travelling along the path 12) excited by the ultrasonic beam incident to the sample at the critical angle $\theta c$. As the sample 6 approaches the transducer 16, the time for which the leaky reradiated wave passes through the sample 6 increases and the phase difference between the vertical reflected wave and the leaky reradiated wave varies accordingly. The periodicity of this curve depends upon the properties of the sample. By measuring the dip interval $\Delta Z$ in FIG. 4, the speed of the leaky elastic surface wave in the sample 6 can be obtained through calculation. The relation between the period $\Delta Z$ and the velocity of sound is given approximately by the following equations:

$$\Delta Z = V_l / \{2f(1 - \cos\theta)\} \quad (1)$$

$$\theta = \sin^{-1}(V_l / V_s) \quad (2)$$

where $V_l$ is the velocity of a longitudinal wave, $V_s$ is the velocity of the leaky elastic surface wave and f is the ultrasonic frequency used.

Therefore, the acoustic characteristics (the velocity of sound, the propagation attenuation, etc.) of the sample 6 can be obtained quantitatively by analyzing the V(z) curve. So, measurement by the arrangement shown in FIG. 3 is called quantitative measurement of the acoustic characteristics of a sample by an ultrasonic microscope. Furthermore, the sound velocity measurement based on the V(z) curve has the feature that the acoustic characteristics of a minute part of the sample could be detected through use of the conically focused (point-focus) ultrasonic beam. But, since the beam component spreads in all directions about the beam axis owing to the symmetrical configuration of the beam, when the sample has anisotropy about the Z axis, anisotropy dependent upon the direction of wave propagation cannot be detected and the velocity of sound is measured as an average value.

In view of this, there has been proposed, for precise quantitative measurement inclusive of anisotropy, an ultrasonic microscope in which the surface of the acoustic lens 11 facing the sample 6 is formed as a concave face forming a part of a cylindrical surface, thereby producing a linearly focused ultrasonic beam, i.e. a line-focus ultrasonic beam 17l for irradiating the sample, as shown in FIG. 5 (see Japanese Pat. Appln. No. 107402/81 or U.S. magazine IEEE, 1981, Ultrasonics Symposium, Nos. 552–556). This microscope also records the V(z) curve while moving the sample 6 in the Z-axis direction as in the case of using the above-mentioned conically focused (point-focus) ultrasonic beam. The relation between the dip interval $\Delta Z$ of the V(z) curve and the velocity of the leaky elastic surface wave in the sample 6 is exactly the same as described previously in connection with the case of employing the conically focused ultrasonic beam.

For determining the velocity of sound by such measuring methods as described above, it is necessary that the dips in the V(z) curve appear at regular intervals. In general, however, in the case where a plurality of leaky elastic surface wave modes participate in the interference phenomenon of waves in the V(z) curve, the dip interval and the waveform of the V(z) curve are irregular. In such a case, the dip period $\Delta Z$ cannot simply be obtained with accuracy from the curve, making it difficult to measure the velocity of the leaky elastic surface wave from the V(z) curve.

With a view to extracting accurate acoustic information of the sample from such a deformed V(z) curve, there has recently been proposed an ultrasonic microscope apparatus which is equipped with a function of making an analysis through utilization of a waveform analysis process, such as the Fourier transformation, on the basis of the theory that "a complex V(z) curve obtainable from a sample in which a plurality of leaky elastic surface wave modes exist can be considered as a superimposition of V(z) curves each obtainable on the assumption that each of the respective modes exists singly in the sample (Japanese Pat. Appln. No. 058368/83 and European Patent Publication No. 121890).

Such measurement as mentioned above is to extract information on the velocity of sound which forms a part of all information on the elastic properties of the sample contained in the V(z) curve. The interference amplitude and the shapes of dips in the V(z) curve are greatly affected as well by the propagation attenuation of the leaky elastic surface wave which participates in the interference. Accordingly, by measuring the propagation attenuation of one or more leaky elastic surface waves which take part in the formation of the V(z) curve, it is possible to learn the complex acoustic impedance, surface state, and internal structure of the sample. For determining the propagation attenuation of the leaky elastic surface wave from the V(z) curve, there has been proposed a method which estimates the attenuation by comparing the depths of dips or the magnitude of the interference amplitude in the V(z) curve with those of the V(z) curve obtained by theoretical calculations. Another conventional method is to determine, through the aid of a computer, the propagation attenuation from the inclination, to the Z axis, of an interference curve $V_I(z)$ obtained by subtracting a reference signal curve $V_R(z)$—dependent upon the shapes of the ultrasonic transducer element and the acoustic lens— from the V(z) curve Japanese Pat. Appln. No. 083428/83 or the aforementioned European patent publication gazette).

Incidentally, as a method for directly measuring the attenuation of the amplitude of the leaky radiated wave relative to the distance of its travel in the Z-axis direction, eliminating its interference with the vertical reflected wave which appears in the V(z) curve, it has been proposed to perform the measurement, eliminating the center axis component of the focused ultrasonic beam or the component which will make the vertically reflected wave by attaching a sound absorber 15 to the acoustic lens 11 centrally thereof facing the sample as shown in FIG. 6A, or dividing the ultrasonic transducer element 16 into two transducer elements 16a and 16b spaced apart so as to establish a sound field suitable for the measurement as depicted in FIG. 6B. Also there has been proposed a method which separates the vertical reflected wave in terms of time through use of extremely short ultrasonic pulses and measures the velocity of sound from the time difference between the received vertical reflected wave and leaky radiated wave and the attenuation from their amplitude variations.

For the detection of anisotropy there has been proposed a method utilizing such an ultrasonic transducer structure as illustrated in FIGS. 7A and 7B. According to this method, the acoustic lens 11 is formed columnar, two semicircular transducer elements 16a and 16b are mounted on one end face of the lens and the other end face is formed as a concave spherical lens face so that two point-focus (conically focused) ultrasonic beams 17a and 17b, and the components of the beams 17a and 17b are detected that are related to the velocity of sound in the direction of their arrangement (Appl. Phys. Lett. 42(5), Mar. 1, 1983, pp. 431–415, "Directional acoustic microscopy for observation of elastic anisotropy", for instance).

By the way, the periodicity of the V(z) curve results from the interference between the two waves shown in FIG. 2, i.e. the reflected wave from the vicinity of the Z-axis (the vertical reflected wave) and the reradiated wave of the leaky elastic surface wave into liquid sound field (the leaky radiated wave). The above-mentioned conventional ultrasonic microscopes possess such disadvantages as follows:

(1) The intensity of the vertical reflected wave depends upon the elastic property of the sample surface 6a and a sufficient reflection intensity for interference cannot be obtained in some cases. For instance, in the case where the sample 6 has a laminar structure, when the acoustic impedance of the liquid sound field medium 4 and the acoustic impedance of the material forming the layer of the sample 6 are matched in relation to the thickness of the layer, ultrasonic waves may sometimes enter deep into the sample 6, diminishing the intensity of the vertical reflected wave. In some cases, reflected waves or interference waves from the inside of the sample 6 may get mixed in the vertical reflected wave. When the sample 6 is a high molecular material or living tissue as well, its acoustic impedance is so low that the intensity of the vertical reflected wave decreases.

(2) Since the vertical reflected wave is a focused beam, the reflection intensity of ultrasonic waves is maximum when the sample surface 6a is at the focal point $F_p$ of the beam. As the sample 6 approaches the focusing ultrasonic transducer 3, incident waves near the Z-axis (the beam center axis) become slightly inclined thereto and reflected waves become out-of-phase in the plane of the transducer 16, by which the intensity of the vertical reflected wave abruptly decreases, resulting in the accuracy of measurement of the dip interval $\Delta Z$ being impaired. As the sample 6 moves closer to the focusing ultrasonic transducer 3, the vertical reflected wave comes to be composed of only reflected components proximate to the Z-axis. This, coupled with the diffusion of the reflected beam, appreciably reduces the intensity of the vertical reflected wave, making it difficult to obtain a sufficient intensity for interference. In addition, this effect varies with the shape of the lens and the elastic property of the sample.

Also in the case of employing, for the detection of anisotropy, the focusing ultrasonic transducer depicted in FIG. 7, the problem of such insufficient intensity of the vertical reflected wave still remains unsolved, since the V(z) curve is obtained utilizing, as the vertical reflected wave, the reflected wave components from the vicinity of the Z-axis which result from such spreading of the beam as indicated by the broken lines.

(3) It is preferable, for the interference, that the pulse duration of the pulse-modulated wave produced by the high-frequency pulse generator 1 be long, but the pulse width is limited primarily for the necessity of signal separation from an unnecessary echo and so forth. On this account, according to the velocity of the leaky elastic surface wave in the sample 6, the leaky radiated wave may lag far behind the vertical reflected wave in reaching the transducer element 16, failing to produce the required interference effect. These problems concerning the vertical reflected wave exert influence upon the interference effect, and hence will seriously impair the accuracy in measuring the velocity of sound and the propagation attenuation from the interference interval and the depths of dips appearing in the V(z) curve.

(4) Next, the method of comparing the V(z) curve with that obtained by theoretical calculations for measuring the propagation attenuation involves the necessity of conducting cumbersome calculations for each sample, in addition to the disadvantage that the V(z) curve itself has the above-mentioned problems concerning the vertical reflected wave, and no required calculations are impossible for a sample of an unknown physical constant. The method of extracting the interference curve $V_I(z)$ from the V(z) curve through use of a computer calls for complex expensive computer and associated apparatus. Besides, the reference signal curve $V_R(z)$ differs with acoustic lenses and samples as referred to previously in (2) and has to be obtained each time, causing inconvenience to the measurement. It is well-known in the art that the method involving no interference between the leaky radiated wave and the vertical reflected wave is theoretically inferior, in accuracy, to the interference method.

(5) The ultrasonic microscope employing the line-focus ultrasonic transducer, as depicted in FIG. 5, can excite the leaky elastic surface wave ideally in a specified direction alone and detect its leaky radiated wave, and hence is capable of obtaining information about the anisotropy of the sample. With this method, however, it is impossible to obtain a two-dimensional image reflecting anisotropy in each grain of a polycrystalline material, such as ceramics, and the V(z) curve in each direction. In other words, the point-focus ultrasonic transducer is absolutely necessary for obtaining the anisotropy information in each grain. But an ultrasonic microscope which employs the point-focus ultrasonic transducer divided into two transducer elements, as depicted in FIG. 7, has the following problems yet to be solved.

That is, the production of contrast in an ultrasonic microscopic image obtainable with the ultrasonic microscope using the focusing ultrasonic transducer, as depicted in FIG. 7, is also in this case, the result of interference between the reflected wave from the vicinity of the Z-axis (the vertical reflected wave) and the reradiated wave of the leaky elastic surface wave (the leaky radiated wave). This imposes various problems concerning the vertical reflected wave. Since the transducer 16 is divided into two elements, the intensity of the vertical reflected wave decreases. In addition, the problems referred to previously in (1) and (2) are also encountered and the reduction of the intensity of the vertical reflected wave will decrease the contrast in the ultrasonic microscopic image, deteriorating the image quality. Besides, the problem mentioned above in (3) remains unsolved as well in this case, too.

SUMMARY OF THE INVENTION

According to the present invention, high-frequency pulses are supplied to a transmitting ultrasonic transducer to cause it to excite a leaky elastic surface wave in the surface of a sample, an electric reference signal is created by a high-frequency pulse generator which generates the high-frequency pulses, and the reference signal is mixed with the output signal of a receiving ultrasonic transducer.

The receiving ultrasonic transducer receives, as a focused ultrasonic beam for reception, the leaky elastic surface wave which propagates in the sample surface and are reradiated therefrom (the leaky radiated wave); the receiving transducer is so designed as not to receive the vertical reflected wave. To this end, the intersecting points of the center axes of the transmitting and receiving ultrasonic transducers and the surface of the sample are spaced apart and the angle of each ultrasonic beam to the sample surface and the beam angular aperture are specified.

A mixer is to obtain an output which is responsive at least to the phase difference between the reference signal and the received signal; if necessary, a mixer which produces an output responsive to their amplitude difference as well is employed. A relative phase changing means is provided by which the phases of the reference signal and the received signal, which are applied to the mixer for obtaining a signal corresponding to the aforementioned V(z) curve, are changed relative to each other. The relative phase changing means is, as in the prior art, a drive means by which a holder for holding the sample and the both transmitting and receiving ultrasonic transducers are moved relative to each other in a direction substantially perpendicular to the sample surface. Alternatively, use is made of a drive means by which one of the transmitting and receiving ultrasonic transducers and the sample holder are moved relative to each other in the direction of arrangement of the intersecting points of the center axes of the both transducers and the sample surface. It is also possible to utilize, as the relative phase changing means, a variable phase shifter which changes the phase of any one of the reference signal which is applied to the mixer, the carrier of the high-frequency pulses which are provided to the transmitting ultrasonic transducer, and the received signal which is fed to the mixer.

For displaying the signal corresponding to the V(z) curve, the abscissa of a display is swept in response to relative phase variations by the relative phase changing means and at the same time the sweep is changed in the ordinate direction in accordance with the output of the mixer.

In the case of actuating the drive means, the phase of any one of the reference signal, the received signal, and the carrier of the high-frequency pulses is controlled by the variable phase shifter in association with the movement of the drive means so as to maintain a fixed phase difference between the reference signal and the received signal, by which the propagation attenuation of the leaky elastic surface wave in the sample surface can be measured. In this instance, it is possible to change the amplitude level of any one of the reference signal, the received signal, and the high-frequency pulses by controlling a level regulator in association with the above-said movement in a manner to compensate for an attenuation in the sound field medium between the both transmitting and receiving ultrasonic transducers and the sample.

An ultrasonic microscopic image is obtained by moving the sample holder and the both transmitting and receiving ultrasonic transducers two-dimensionally by the drive means in parallel to the sample surface, by scanning the display screen of a display two-dimensionally in synchronism with the two-dimensional movement, and by displaying the output of the mixer at each point during the two-dimensional movement. In the case of obtaining either the ultrasonic microscopic image or the signal corresponding to the V(z) curve, information about the anisotropy of the sample can be obtained by rotating the both transmitting and receiving ultrasonic transducers and the sample holder by a rotating means relative to each other in parallel to the sample surface.

The transmitting and receiving ultrasonic transducers may be produced separately or may be formed with the acoustic lens common to them. In the case where the acoustic lens is formed common to the both transducers, its face opposite the sample is made a spherical or cylindrical concavedly curved face and the face opposite from this concaved one is made a spherical or cylindrical convexedly curved face correspondingly, and transmitting and receiving transducer elements are disposed apart on the convexedly curved face.

It is also possible to interconnect the transmitting and receiving ultrasonic transducers and connect this connection point via a duplexer to the high-frequency pulse generator and the mixer so that the both transducers are concurrently driven by the high-frequency pulses and their received signals are provided to the mixer at the same.

BEST MODE FOR CARRYING OUT THE INVENTION

Figure 8:
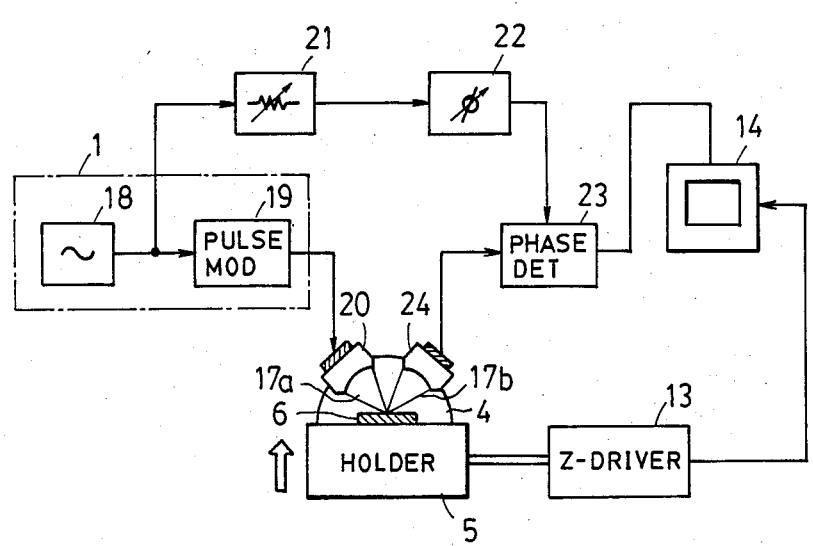
FIG. 8 is a block diagram illustrating an embodiment of the present invention applied to a microscope for obtaining the V(z) curve.

FIG. 8 illustrates an embodiment of the surface ultrasonic wave interference microscope of the present invention. In the high-frequency pulse generator 1 a high-frequency signal from a high-frequency generator 18 is pulse modulated by a pulse modulator 19. The high-frequency signal thus pulse modulated is provided, as a burst-like signal or high-frequency pulses, to a transmitting ultrasonic transducer 20, exciting it. On the other hand, the output of the high-frequency generator 18 is branched to an attenuator 21 serving as a level regulator, wherein it is regulated to a suitable level, thereafter being applied as a reference signal via a phase shifter 22 to a phase detector 23 which acts as a mixer. The electric output (a received signal) of a receiving ultrasonic transducer 24 for receiving a leaky elastic surface wave is phase detected by the reference signal from the phase shifter 22 in the phase detector 23, that is, the phase difference between the received signal and the reference signal is detected. The detected output is applied as a display signal to an oscilloscope 14. The sample 6 disposed in the liquid sound field medium 4 is placed on the sample holder 5 and a Z-direction movement control signal is provided to an X-axis scanning signal terminal of the oscilloscope 14 from a Z-direction driver 13 which moves the sample holder 5 along the Z-axis. The Z-direction driver 13 may be such as set forth in the aforementioned European patent publication gazette.

Figure 9:
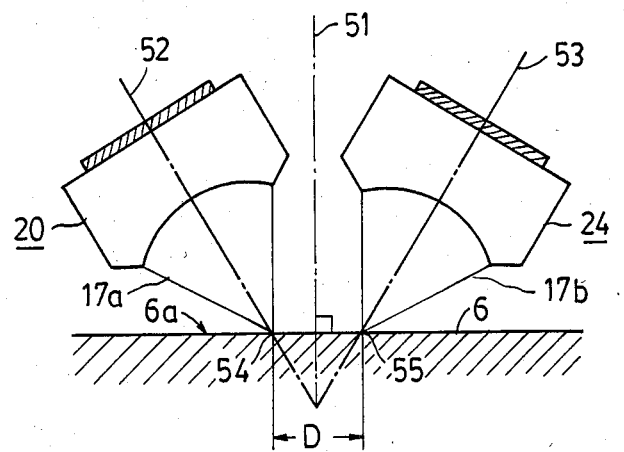
FIG. 9 is an enlarged diagram showing ultrasonic transducers used in FIG. 8.

The sample 6 is irradiated by the focused ultrasonic beam 17a from the transmitting ultrasonic transducer 20 disposed with its center axis 52 inclined to the normal 51 to the sample surface (see FIG. 9). That is, the transmitting ultrasonic transducer 20 is excited by the high-frequency pulses 2 from the high-frequency pulse generator 1, the focused ultrasonic beam 17a of the high-frequency pulses is radiated, and the elastic surface wave is excited in the surface of the sample 6 by those components of the focused ultrasonic beam 17a which lie within the critical angle θc and can excite the elastic surface wave which propagates in the sample surface. The receiving ultrasonic transducer 24 is disposed on the leaky elastic surface wave propagation path with its center axis 53 inclined to the normal 51 to the sample 6 in the direction opposite from that in which the transmitting ultrasonic transducer 20 is inclined, and the leaky elastic surface wave is received and detected by the receiving ultrasonic transducer 24. The center axes 52 and 53 intersect under the sample surface 6a and intersecting points 54 and 55 of the center axes 52 and 53 and the sample surface 6a are spaced a distance D apart. The transmitting and receiving ultrasonic transducers 20 and 24 are disposed so that their focal points lie on the sample surface 6a or at the same position. The electric output of the receiving ultrasonic transducer 24 (the received signal) is supplied to the phase detector 23, wherein it is phase detected.

Figure 4:
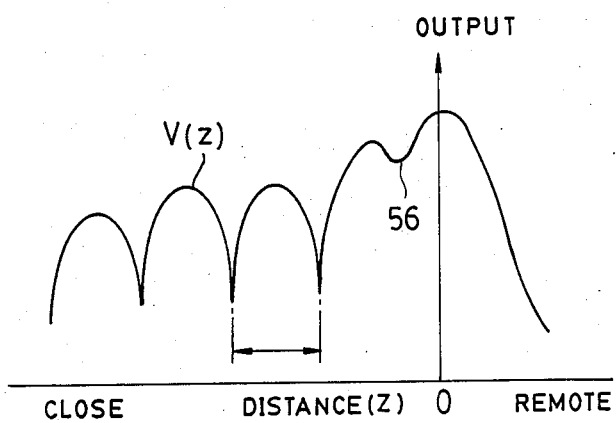
FIG. 4 is a graph showing an example of the V(z) curve obtained with the microscope depicted in FIG. 3.
Figure 10:
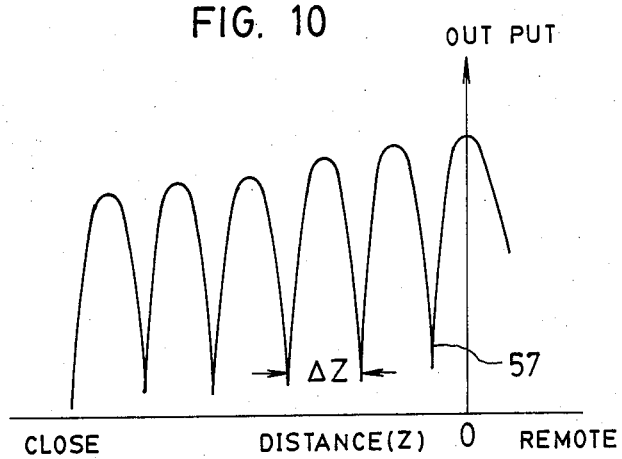
FIG. 10 is a graph showing an example of the V(z) curve obtained with the microscope depicted in FIG. 8.

Now, when moving gently the sample holder 5 in a direction vertical to the sample surface 6a (in the Z-direction), the distance D between the intersecting points 54 and 55 gradually varies, causing gradual variations in the phase difference between the received signal of the leaky elastic surface wave and the reference signal. In consequence, the output of the phase detector 23 becomes maximum when the reference signal and the received signal are in-phase and minimum when they are 180° out-of-phase, thus displaying on the display screen of the oscilloscope 14 an interference curve in which dips appear periodically in response to the variations in the distance Z between the both ultrasonic transducers 20 and 24 and the sample surface 6a, as shown in FIG. 10. FIG. 10 shows that when the sample surface 6a lies at the cofocal position of the both ultrasonic transducers 20 and 24, Z=0 and on the left-hand side of this position the sample surface 6a approaches the transducers 20 and 24. The curve shown in FIG. 10 corresponds to the conventional V(z) curve. In this curve a deep dip 57 appears in the part of the curve of FIG. 4 in which a shallow dip 56 occurs in the neighborhood of Z=0. It is considered that the shallow dip 56 in FIG. 4 occurred for the reason that the intensity of the vertical reflected wave was too high. In the embodiment of FIG. 8, however, the level of the reference signal is fixed, and by adjusting this level with the attenuator 21 to be equal to the level of the received signal, the dips of the interference curve can be made sharp, facilitating the measurement of the dip interval ΔZ. The dip interval ΔZ is given approximately by the following equations:

$$\Delta Z = V_l / 2f\cos\theta \quad (3)$$

$$\theta = \sin^{-1}(V_l/V_s) \quad (4)$$

where $V_l$, $V_s$, and f are the same as those in Eqs. (1) and (2).

Figure 11:
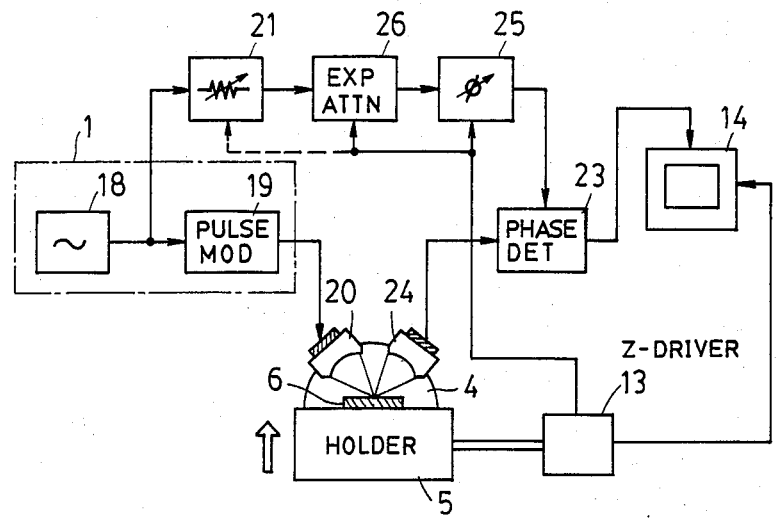
FIG. 11 is a block diagram illustrating an example of the microscope of FIG. 8 modified for enabling the measurement of attenuation as well.

FIG. 11 illustrates another embodiment of the present invention. The phase of the reference signal is varied by a variable phase shifter 25 in accordance with the movement of the sample holder 5 in the Z-axis direction. The dip interval ΔZ can freely be changed by altering the rate of phase variation of the reference signal to the movement of the sample holder in the Z-axis direction. When the phase of the reference signal is fixed, the number of dips in the interference curve (i.e. the curve shown in FIG. 10) is maximum and as the rate of phase variation of the reference signal increases (i.e. the phase shift) the number of dips will decrease. Accordingly, in the case of a sample for which the number of dips in the interference curve is small according to the prior art, the number of dips can be increased, raising the accuracy of measurement of the dip interval ΔZ.

Figure 12:
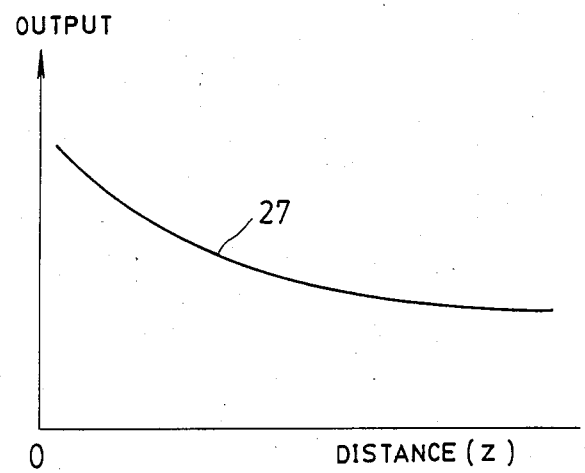
FIG. 12 is a graph showing an example of an attenuation curve measured by the microscope depicted in FIG. 11.

By controlling the variable phase shifter in such a manner that the phase variation of the reference signal corresponds faithfully to the phase variation of the received signal of the leaky elastic surface wave, for example, the both signals are always 180° out of phase, it is possible to obtain, as the output waveform which is to be displayed on the oscilloscope 14, a curve 27 which exponentially smoothly attenuates, as shown in FIG. 12, according to the attenuation of the leaky elastic surface wave. In this instance, however, the phase detector 23 must be able to yield an output which responds to the amplitude of the input signal as well. In FIG. 12, as the distance Z increases to the right, the spacing between the transducers 20 and 24 and the sample surface 6a decreases. The curve shown in FIG. 12 indicates the case where the attenuation factor of the sample 6 is larger than that of the acoustic medium 4. Conversely, when the attenuation factor of the sample 6 is smaller than that of the acoustic medium 4, an exponentially rising curve will be obtained since the attenuation by the sample 6 decreases as it approaches the transducers. The propagation attenuation of the leaky elastic surface wave can be measured from the gradient of the curve shown in FIG. 12. Furthermore, in this embodiment a variable attenuator 26 is employed as the level regulator for exponentially varying the attenuation in accordance with the distance of travel of the sample holder 5 in the Z-axis direction, besides provision is made for arbitrarily changing the attenuation manually (or automatically). The propagation attenuation of the leaky elastic surface wave can be determined by adjusting the attenuation of the attenuator 26 while observing such an exponentially smoothly varying curve 27 as shown in FIG. 12 on the display screen of the oscilloscope 14 and detecting the value of the attenuation when the curve 27 is nullified relative to the distance Z. In this case, it is also possible, if necessary, to vary the attenuation of the other variable attenuator 21 exponentially in accordance with the distance of movement of the sample holder 5 in the Z-axis direction, thereby compensating for the attenuation of the received signal in the acoustic field 4 which accompanies the movement of the sample holder 5.

The exponential variation of the level can be achieved by a technique similar to what is called an STC technique which is applied to various ultrasonic measuring instruments, such as an ultrasonic level meter and a sonar, a radar, etc. so that they are synchronized with the emission of a pulse and raises their sensitivity with the lapse of time. To perform this, it is necessary only to employ, for example, an arrangement which creates a control signal through utilization of the charging or discharging characteristic of an CR time constant circuit and regulates its time constant or the level of voltage thereto as required.

Figure 13:
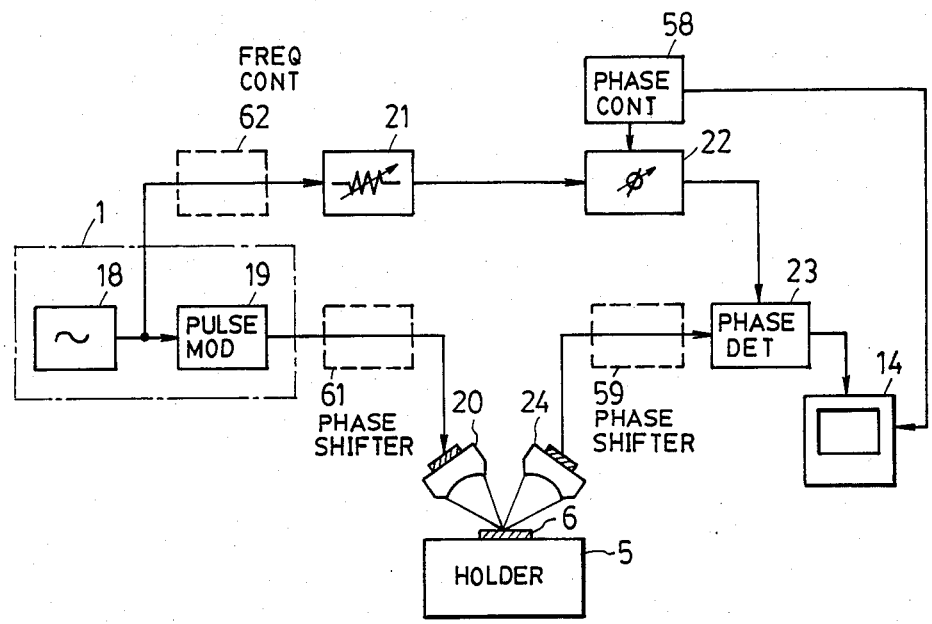
FIG. 13 is a block diagram illustrating another embodiment of the present invention for obtaining a curve corresponding to the V(z) curve in the state in which transducers and a sample holder are fixed.

Although in the above the distance between the ultrasonic transducers 20 and 24 and the sample 6, that is, the distance in the Z-axis direction, is varied for causing variations in the phase difference between the reference signal and the received signal which are supplied to the mixer (or the phase shifter) 23, it is also possible to fix the above distance. In such a case, it is necessary only to provide a phase controller 58, for instance, as depicted in FIG. 13, so that the variable phase shifter 22 is controlled by a control signal from the phase controller 58 to gradually change the phase of the reference signal and at the same time the abscissa of the oscilloscope 14 is controlled in synchronism with the phase control. Alternatively, it is also possible to provide a variable phase shifter 59 or 61 at the input side of the phase detector 23 or at the output side of the high-frequency pulse generator 1, as indicated by the broken lines, so that the variable phase shifter is controlled by the control signal from the phase controller 58, causing the received signal or the carrier of the high-frequency pulses to undergo gradual phase variations. Incidentally it is necessary in the embodiment of FIG. 13 to preknow the distance D between the intersecting points 54 and 55 of the center axes of the both ultrasonic transducers 20 and 24 and the sample surface 6a (FIG. 9). Moreover, in this instance, the attenuation characteristic cannot be measured.

Figure 14:
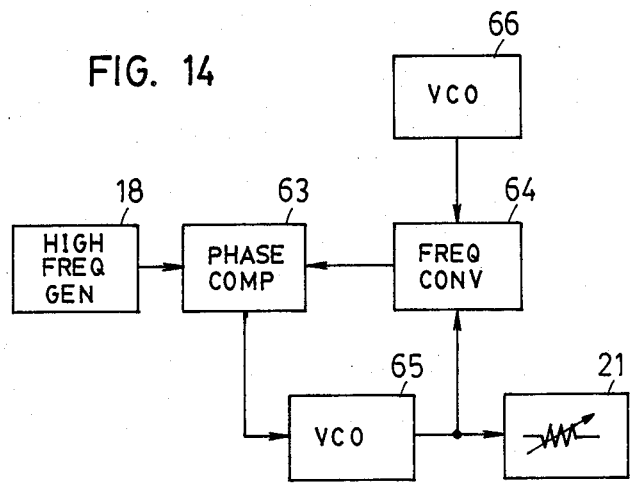
FIG. 14 is a block diagram illustrating a specific operative example of a variable frequency controller 62 used in FIG. 13.

In order to change the phases of the signals which are supplied to the phase detector 23, the frequencies of the reference signal and the carrier of the high-frequency pulses may also be varied substantially continuously relative to each other by steps of several to several tens of hertzs, for instance. This can be achieved, for example, by providing a variable frequency controller 62 at the input side of the variable attenuator 21, as indicated by the broken line in FIG. 13. For example, as shown in FIG. 14, the variable frequency controller 62 can be arranged such that the output of the high-frequency wave generator 18 is supplied to a phase comparator 63, wherein it is phase compared with the output of a frequency converter 64, the oscillation frequency of a voltage-controlled variable oscillator 65 is controlled by the phase-compared output, and the output of the voltage-controlled variable oscillator 65 is frequency converted by the frequency converter 64, along with the output of a variable frequency oscillator 66. By selecting the oscillation frequency of the voltage-controlled oscillator 66 twice as high as the frequency of the high-frequency oscillator 18 and varying it, for instance, by steps of one hertz, the oscillation frequency of the voltage-controlled variable oscillator 65 can be varied by steps of one hertz with respect to the frequency of the high-frequency oscillator 18, and its output is provided to the variable attenuator 21.

Figure 15:
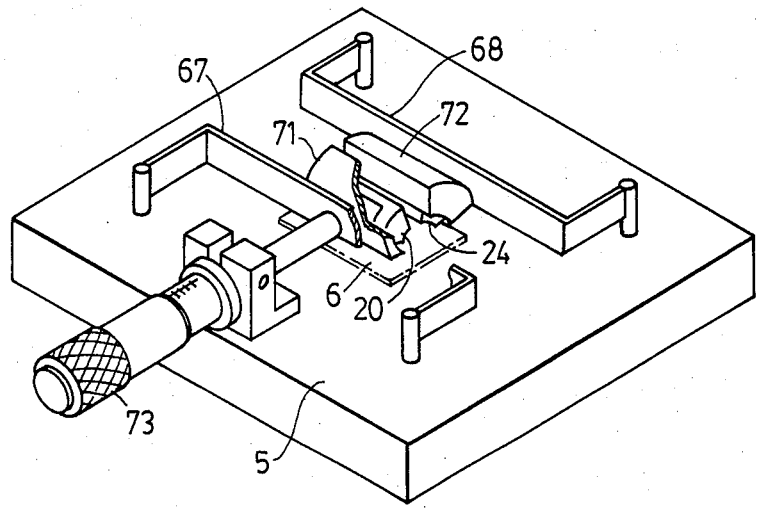
FIG. 15 is a perspective view, partly cut away, illustrating an example of a drive device for moving the transducer 20 in the direction of arrangement of the transducers 20 and 24.

Also it is possible to move one of the ultrasonic transducers 20 and 24 and the sample holder 5 relative to each other in the direction of arrangement of the intersecting points 54 and 55 of the center axes of the transducers 20 and 24 and the sample surface 6a, instead of moving the both ultrasonic transducers 20 and 24 and the sample holder 5 in the Z-axis direction. To perform this, such an arrangement as shown in FIG. 15 is employed in which band-shaped plate springs 67 and 68 are held on the sample holder 5 with their faces opposite each other, cases 71 and 72 are attached to the opposed faces of the plate springs 67 and 68, and the transmitting and receiving ultrasonic transducers 20 and 24 are disposed between the cases 71 and 72. In the illustrated embodiment a concave transducer for creating the line-focus beam is used as each of the transducers 20 and 24 but a point-focus beam transducer may also be utilized. The intermediate portion of the one plate spring 67 is moved precisely, by means of a micrometer 73 fixedly secured on the sample holder 5, in parallel to the top surface of the sample holder 5, by which the distance between the both transducers 20 and 24 is controlled. In synchronism with this movement the abscissa of the oscilloscope 14 is swept. In this case, the attenuation factor can also be measured by controlling the phase shifter 25 in association with the control of the distance between the transducers 20 and 24 in the same manner as in the example shown in FIG. 11.

Figure 1:
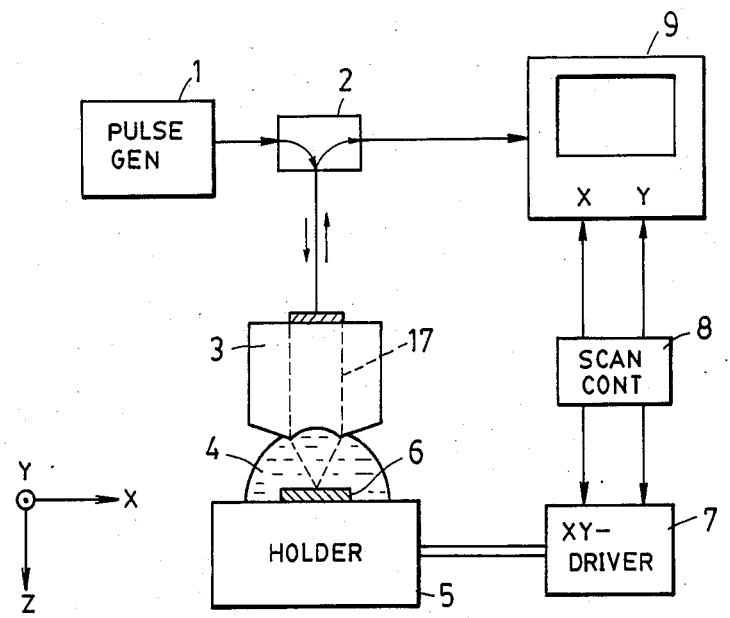
FIG. 1 is a block diagram illustrating a conventional surface ultrasonic wave interference microscope for obtaining an ultrasonic microscopic image.
Figure 2:
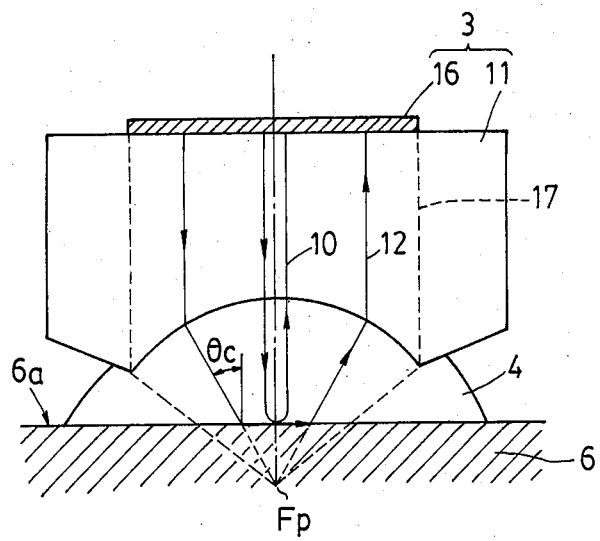
FIG. 2 is a cross-sectional view for explaining the generation of the vertical reflected wave and the leaky radiated wave in the microscope depicted in FIG. 1.
Figure 3:
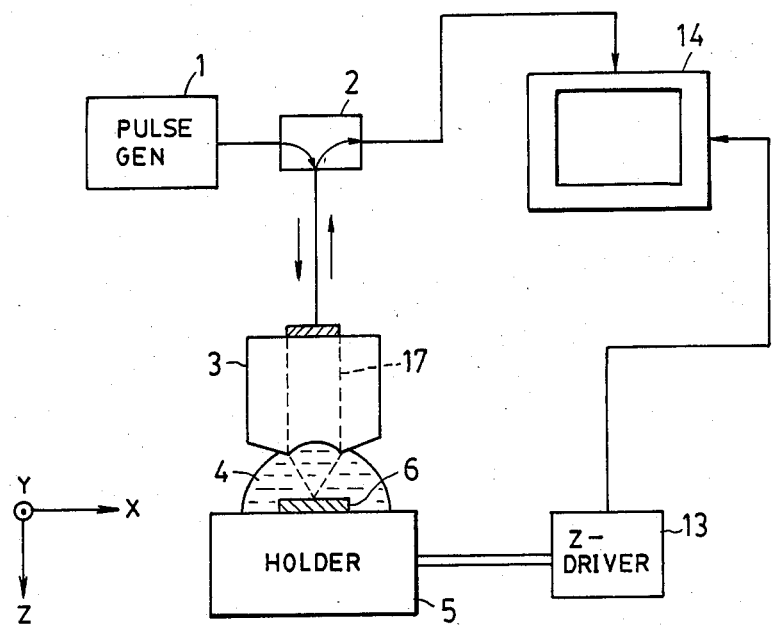
FIG. 3 is a block diagram illustrating a conventional surface ultrasonic wave interference microscope for obtaining the V(z) curve.
Figure 16:
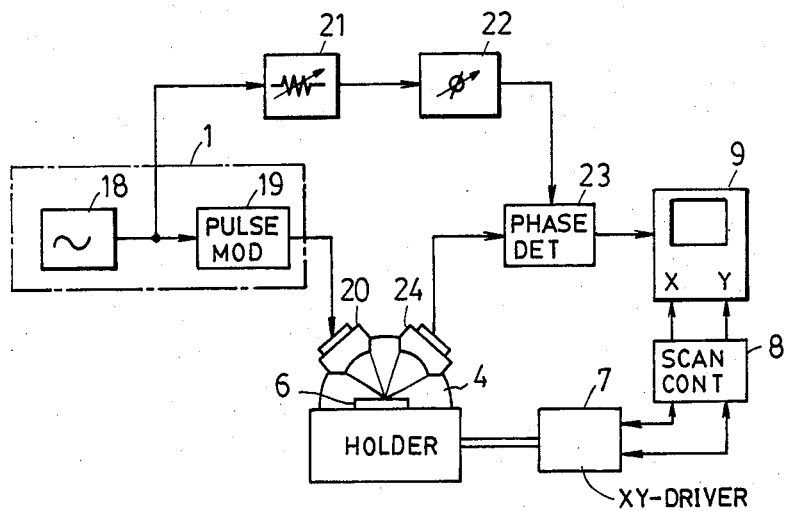
FIG. 16 is a block diagram illustrating another embodiment of the present invention applied to a surface ultrasonic wave interference microscope which produces an ultrasonic microscopic image.

Next, a description will be given, with reference to FIG. 16, of the case of obtaining an ultrasonic microscopic image (i.e. the case of performing pictorial measurement). In this instance, the sample holder 5 is moved by the XY-direction driver 7 in the X- and Y-directions for two-dimensional scanning of the sample surface 6a in the X-Y plane, as described previously in connection with FIG. 1. In synchronism with this scanning of the sample surface the display screen of the display 9 is scanned two-dimensionally and the output of the phase detector 23 is supplied to a display signal to the display 9. In consequence, an ultrasonic microscopic image is displayed on the display screen of the display 9. The attenuation factor of the leaky elastic surface wave in the sample surface may sometimes differ with locations therein, in which case the contrast of a particular portion of the image being displayed or the contrast of the entire image can be adjusted by a suitable selection of the level of the reference signal relative to the level of the received signal from the receiving ultrasonic transducer 24 through use of the variable attenuator 21. The XY-direction driver 7 may be such as depicted in FIG. 9 of the aforementioned European patent publication gazette.

Figure 5:
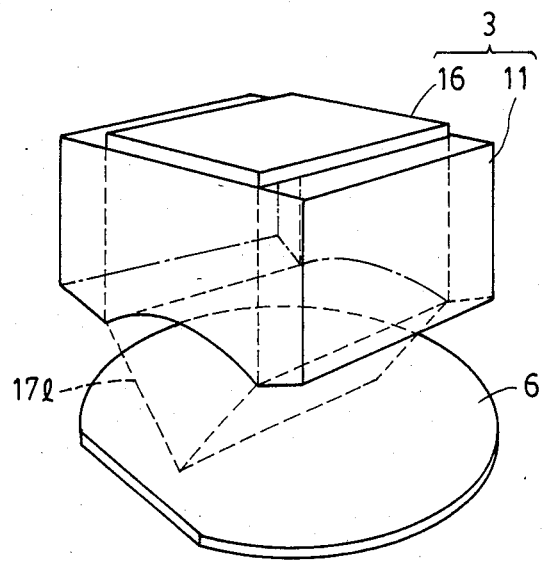
FIG. 5 is a perspective view showing a lens type line-focus ultrasonic transducer.
Figure 17:
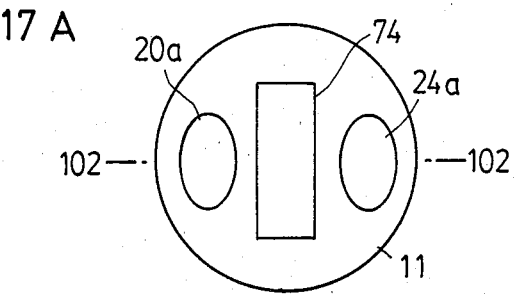
FIG. 17 is a diagrammatic representation of an example of a point-focus ultrasonic transducer structure in which the transducers 20 and 24 are formed as a unitary structure with each other, FIG. 17A being its plan view and FIG. 17B its cross-sectional view taken on the line 102—102 in FIG. 17A.
Figure 17:
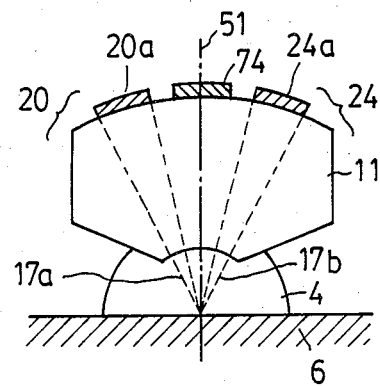

While the above embodiments, except the one in FIG. 15, all employ the lens type ultrasonic transducer in which transducer elements 20a and 24a are mounted in a plane on the acoustic lens, it is a matter of course to use concave transducers. In this instance, it is also possible to form the acoustic lens as a unitary structure common to the both transmitting and receiving transducer elements. For example, as illustrated in FIG. 17, one end face of the acoustic lens 11 (usually made of sapphire, fused quartz, or the like) is formed into a convex face which forms a part of a spherical surface, the pair of transducers 20a and 24a are mounted on the convex face, the other end face of the acoustic lens 11 is scooped out to form a concave face which forms a part of a spherical surface, and the transducer assembly is disposed with the concave face opposed to the sample 6. The acoustic lens is machined so that the spherical surfaces forming its convex and concave faces, respectively, have the same radial direction, and is disposed so that the radial direction agrees with the normal 51 of the sample surface 6a. The transducer element 20a and the acoustic lens 11 build up the transmitting ultrasonic transducer 20 and the transducer element 24a and the acoustic lens 11 the receiving ultrasonic transducer 24, by which the focused ultrasonic beam 17a for transmission and the focused ultrasonic beam 17b for reception are created. It is preferable that a sound absorber 74, for instance, a high molecular adhesive, be disposed between the transducer elements 20a and 24a. The convex and concave faces of the acoustic lens 11 need not always be concentric but, for example, the radius of curvature of the convex face is selected greater than that of the concave face so that a focused ultrasonic beam of high resolution is produced. Also it is possible, in FIG. 17, that the convex face of the acoustic lens 11 for the attachment thereon of the transducer elements 20a and 24a and the concave face opposite the sample are each formed as a part of one of cylindrical faces of parallel axes, not as a part of the spherical surface, that is, the acoustic lens 11 in FIG. 17B is formed as a block which extends normal to the plane of the paper while retaining its cross section unchanged so that the transmitting and receiving ultrasonic transducers 20 and 24 individually create line-focus ultrasonic beams. Such a line-focus or point-focus type concave transducer as shown in FIG. 15 or such a lens type line-focus ultrasonic transducer as shown in FIG. 5 may be applied to each of the transmitting and receiving ultrasonic transducers 20 and 24 in the foregoing embodiments except the one in FIG. 15.

Figure 18:
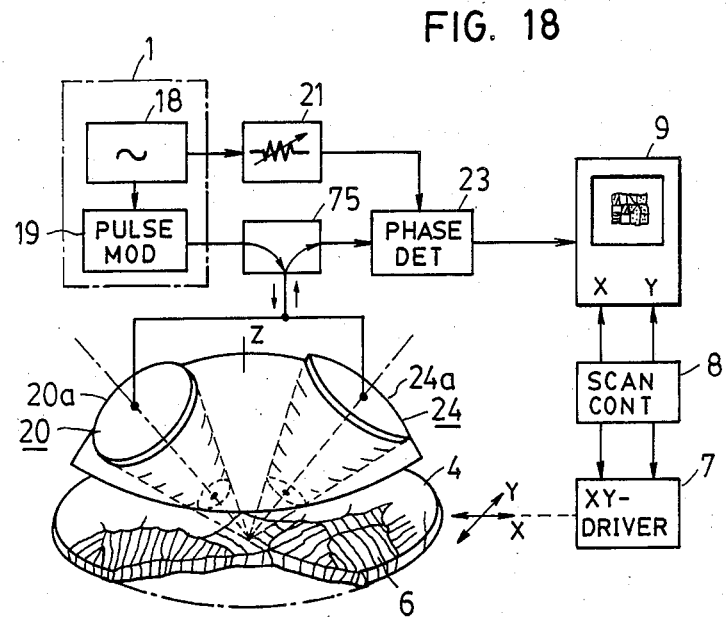
FIG. 18 is a block diagram illustrating another embodiment of the present invention which concurrently excites the transducers 20 and 24.
Figure 19:
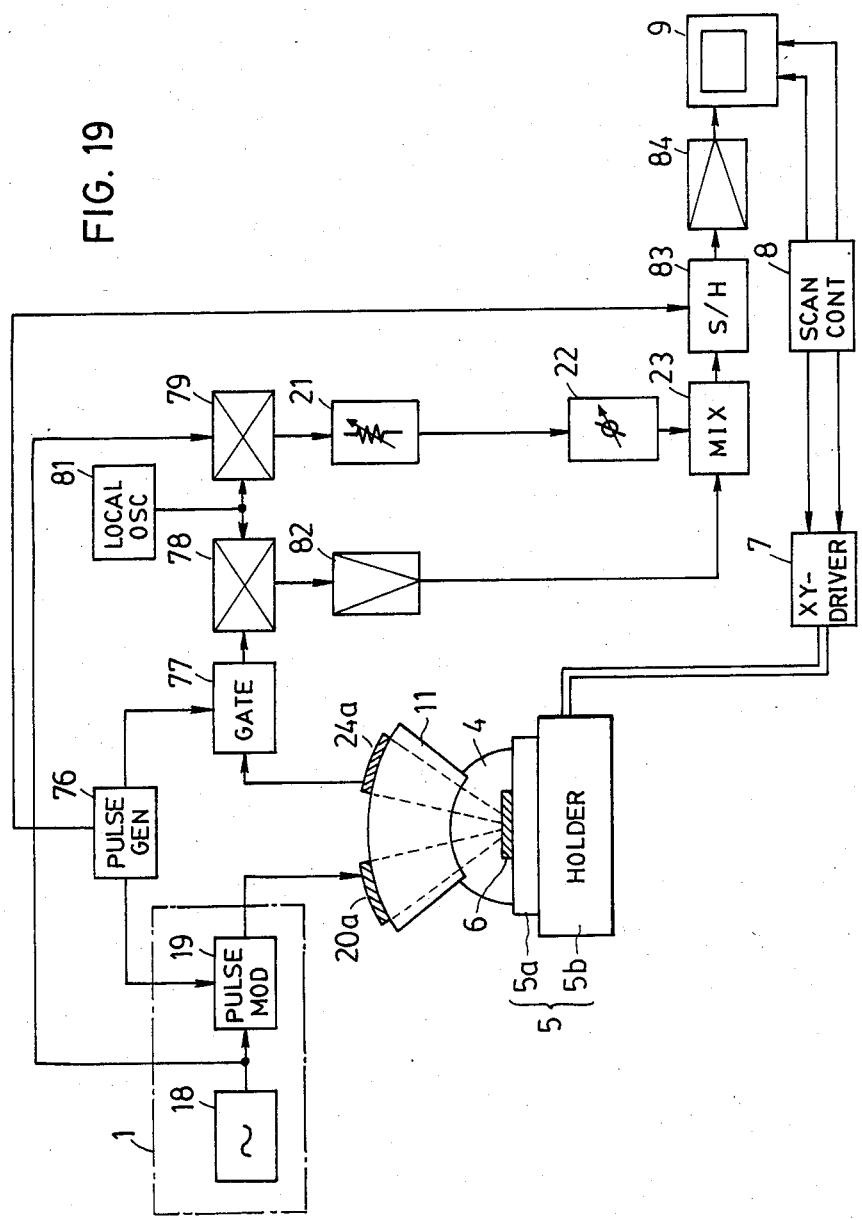
FIG. 19 is a block diagram illustrating another embodiment of the present invention in which the sample is turnable in the XY plane.

Although in the above the high-frequency pulses are supplied solely to the transmitting ultrasonic transducer 20, it is also possible to adopt an arrangement in which the high-frequency pulses are provided to the receiving ultrasonic transducer 24 as well and the outputs of the both ultrasonic transducers are applied to the mixer 23, thereby providing for increased sensitivity. FIG. 18 illustrates an example of this arrangement, which employs the ultrasonic transducer depicted in FIG. 17 and in which the transducer elements 20a and 24a are interconnected and the connection point is connected to a duplexer 75 such as a directional coupler, circulator, or the like. The duplexer 75 is connected to the output side of the high-frequency pulse generator 1 and the input side of the mixer 23. The high-frequency pulses from the high-frequency pulse generator 1 are applied via the duplexer 75 to the ultrasonic transducers 20 and 24, exciting them concurrently. Ultrasonic beams from the both transducers 20 and 24 are simultaneously applied to the sample 6 to excite therein leaky elastic surface waves at the same time, the leaky elastic surface waves propagate toward each other, their leaky radiated waves are received by the transducers 20 and 24, respectively, and these received signals are both provided via the duplexer 75 to the mixer 23 at the same time. In the other respects, this embodiment is identical with the foregoing embodiments. In FIG. 18 the sample 6 is a polycrystalline material such as ferrite or piezoelectric ceramics. In the case of measuring such a polycrystalline sample 6, it is difficult, in general, to create a line-focus ultrasonic beam of a width smaller than its grain; so a point-focus ultrasonic beam is used for detecting the acoustic characteristics of each grain. In addition, when anisotropy is present in the grain, the anisotropy for each grain can also be measured by conducting measurements from different directions along the surface of the sample. From this point of view, it is preferable to make provision for turning the ultrasonic transducers 20 and 24 and the sample holder 5 about the Z-axis relative to each other. FIG. 19 illustrates its example, in which the upper portion of the sample holder 5 is formed as a turntable 5a, on which the sample 6 is placed. The turntable 5a is turnable about the Z-axis relative to the body 5b of the sample holder 5 and this can be achieved by using the means depicted in FIG. 19 of the aforementioned European patent publication gazette, for example. In the example shown in FIG. 19 a pulse generator 76 applies modulated pulses to the pulse modulator 19, creates gate pulses based on the modulated pulses, and controls a gate 77 by the gate pulses to permit the passage therethrough of only the required leaky radiated wave, cutting off unnecessary waves. The received signal having passed through the gate 77 and the high-frequency signal from the high-frequency oscillator 18 are respectively converted by local signals from a local oscillator 81 in frequency converters 78 and 79 into intermediate-frequency signals. The intermediate-frequency received signal is provided via an amplifier 82 to the mixer 23 and the output of the frequency converter 79 is applied as the reference signal to the mixer 23 via the attenuator 21 and the phase shifter 22. The output of the mixer 23 is held by sampling pulses from the pulse generator 76 in a sample-hold circuit 83, the output of which is supplied as a display signal to the display 9 via a video amplifier 84.

With the apparatus illustrated in FIG. 19, the turntable 5a is set in a certain direction (at a certain rotational angular position), an ultrasonic microscopic image is displayed (recorded), the turntable 5a is set in another direction, an ultrasonic microscopic image is obtained, and thereafter similar operations are repeated. In the case of an anisotropic polycrystalline sample, the contrast on the sample surface, even at the same area, changed with the direction of setting the turntable 5a.

Even with samples of the same kind, the velocity of sound and the attenuation characteristic may sometimes slightly differ according to their manufacturing conditions and so on. When dividing the oscillation frequency of the high-frequency oscillator 18 in several steps in the range of, for example, 50 to 400 MHz and obtaining ultrasonic microscopic images at the respective frequencies, subtle differences are observed among them.

Figure 20:
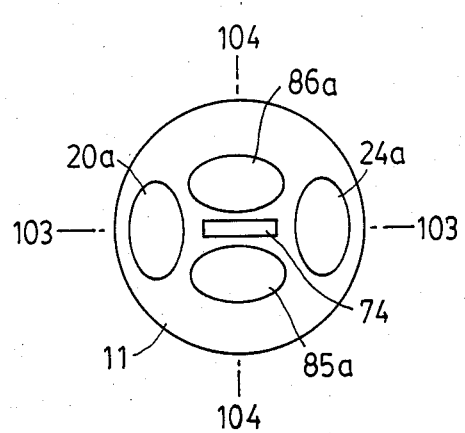
FIG. 20 is a diagrammatic showing of an example of the point-focus ultrasonic transducer structure in which transducers 20, 24, 85, and 86 are formed as a unitary structure with one another, FIG. 20A being its plan view, FIG. 20B its cross-sectional view taken on the line 103—103 in FIG. 20A, and FIG. 20C its cross-sectional view taken on the line 104—104 in FIG. 20A.
Figure 20:
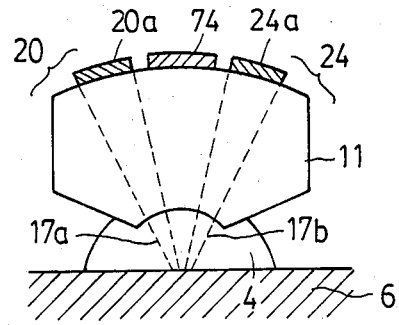
Figure 20:
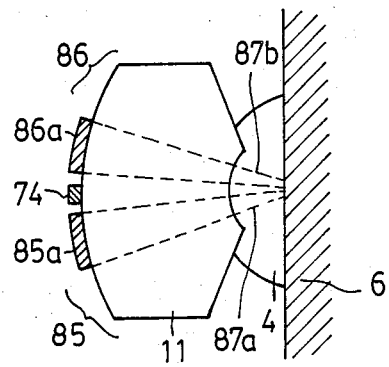

More than two ultrasonic transducers may also be used. For instance, as shown in FIG. 20, transducer elements 85a and 86a are arranged on the convex face of the acoustic lens 11 between the transducer elements 20a and 24a in a direction perpendicular to the direction of arrangement of the transducer elements 20a and 24a in the structure shown in FIG. 17. The transducer elements 85a and 86a and the acoustic lens 11 constitute ultrasonic transducers 85 and 86, respectively, by which focused ultrasonic beams 87a and 87b are produced. In this instance, the transducer elements 85a and 86a are spaced apart a distance smaller than that between the transducer elements 20a and 24a and the angle of intersection of the center axis of each of the focused ultrasonic beams 17a and 17b with the sample surface and the angle of intersection of the center axis of each of the focused ultrasonic beams 87a and 87b with the sample surface are made different from each other, and the transducer elements 20 and 24 and the transducer elements 85 and 86 are selectively changed over by means of a switch in such a manner as to use the former for a sample in which the velocity of the leaky elastic surface wave is low and the latter for a sample in which the velocity of the leaky elastic surface wave is high. With such an arrangement, measurements of various samples in which the velocity of sound varies over a wide range can be achieved without the necessity of exchanging the ultrasonic transducers each time.

It is also possible to employ, in combination, the concave ultrasonic transducer for transmission and the lens type ultrasonic transducer for reception. In the embodiment of FIG. 19 a curve corresponding to the V(z) curve may also be measured by using the Z-direction driver 10 in place of the XY-driver 7 and the oscilloscope 14 as the display 9. Also it is possible to adopt an arrangement in which the sample holder 5 can be controlled to move in either of the XY-direction and the Z-direction for obtaining an ultrasonic microscopic image or the curve corresponding to the V(z) curve, as required.

Figure 21:
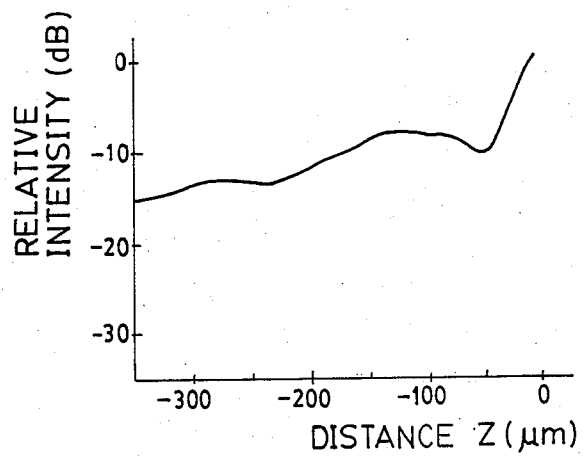
FIG. 21 is a graph showing the results of measurement or the V(z) curve obtained by the ultrasonic microscope of the present invention, with the reference signal held OFF.
Figure 22:
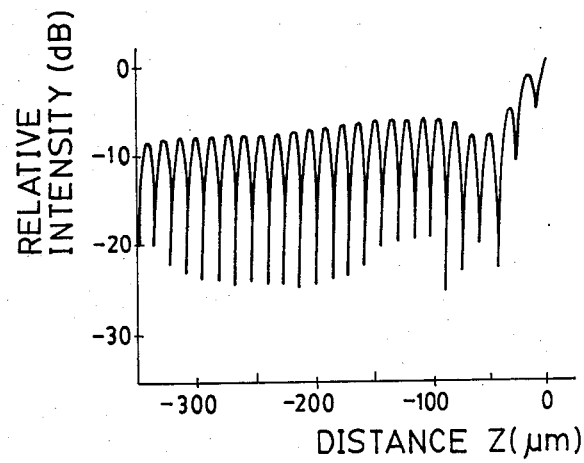
FIG. 22 is a graph showing the V(z) curve obtained, with the reference signal ON, through use of the same ultrasonic microscope as employed for obtaining the curve in FIG. 21.

In the apparatus shown in FIG. 19, the Z-direction driver 10 was used instead of the XY-direction driver, the oscilloscope 14 was used in place of the display 9, the convex and concave faces of the acoustic lens 11 were formed with radii of curvature of 9 and 2.5 cm, respectively, the convex and concave faces were positioned on the concentric spherical surface, the acoustic lens 11 was made of glass, the transducer elements 20a and 24a were each formed by attaching an aluminum electrode to a ZnO film of 5.4 mm in diameter and 29 $\mu$m in thickness, their inner spacing was selected to be 4.6 mm, and their angles to the center were selected to be 30°. The transducers 20 and 24 had a center frequency of 80 MHz or so. As a result of measuring the sound field distribution at 60 MHz, the sound intensity on the Z-axis, at a position more than 100 $\mu$m apart from the transducer, was suppressed below $-25$ dB, as compared with at the focal point. A sheet of fused quartz was used as the sample 6 and the V(z) curve was measured. When no reference signal was applied to the mixer 23, the curve was such as shown in FIG. 21. This curve has no periodic dips, and hence is not an interference curve; namely, the vertical reflected wave was eliminated. When the reference signal was provided to the mixer 23, such as curve as shown in FIG. 22 was obtained. A number of dips appeared periodically. The dip interval $\Delta Z$ obtained from this curve was 13.9 $\mu$m. The velocity of the leaky elastic surface wave calculated supposing that the velocity of sound in the sound medium 4 of water was 1493 m/s (at 23.5° C.) was $3.35 \times 10^3$ m/s. This value substantially agrees with a value, $3.430 \times 10^3$ m/s, calculated from the physical constant of fused quartz.

According to the prior art, in the cases of obtaining the V(z) curve (for a quantitative measurement) and a pictorial measurement for obtaining an ultrasonic microscopic image as well, since the vertical reflected wave not only depends upon the acoustic characteristics of a sample but also is superimposed on waves reflected from the inside of the sample, they exert complex influence on either of the quantitative measurement and the pictorial measurement. In contrast thereto, the present invention eliminates the vertical reflected wave, and hence is free from this problem, permitting the extraction of only information about the leaky elastic surface wave in the sample. At the same time, measuring and signal processing operations also become easy and the measuring time can also be shortened; so the present invention offers a surface ultrasonic wave interference microscope easy to handle. The system which moves the transmitting or receiving ultrasonic transducer and the sample holder relative to each other as shown in FIG. 15 and the system which fixes the transducer and the sample holder as depicted in FIG. 13 are advantageous in the ultra-high frequency band in which the propagation attenuation by the sound field medium 4 imposes a problem, since the distance of propagation in the sound field medium is constant. Furthermore, by properly setting the position of the receiving ultrasonic transducer, reflected waves other than the leaky radiated wave can be eliminated from the beginning.

Moreover, the present invention permits utilization of the zero method for measuring the propagation attenuation of the leaky elastic surface wave, and hence provides a surface ultrasonic wave interference microscope capable of extremely high precision measurements which have been difficult in the past.

Figure 6:
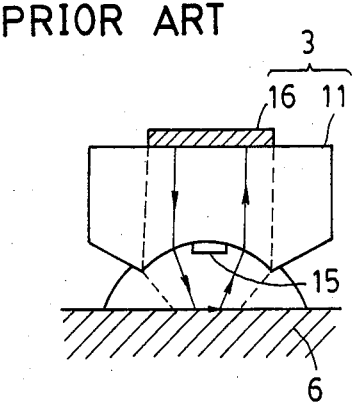
FIGS. 6A and 6B are cross-sectional views illustrating an ultrasonic transducer heretofore employed for directly measuring attenuation of the leaky radiated wave.
Figure 6:
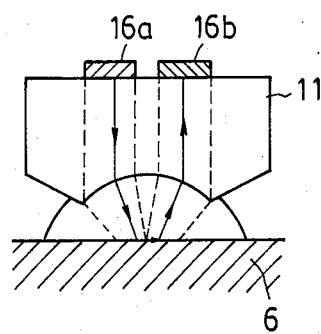
Figure 7A:
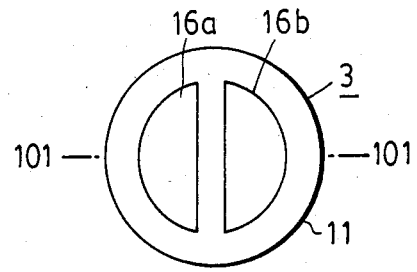
FIG. 7 is a diagrammatic showing of a point-focus ultrasonic transducer heretofore employed for detecting anisotropy, FIG. 7A being its plan view and FIG. 7B a cross-sectional view taken on the line 101—101 in FIG. 7A.
Figure 7B:
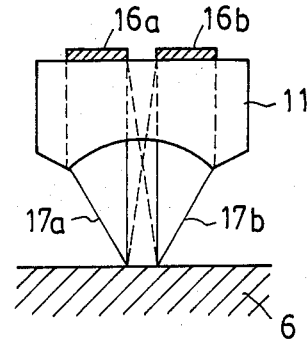

In addition, according to the lens type ultrasonic transducer of such a structure as shown in FIG. 6B, when the distance between the plane transducers 16a and 16b and the concave face of the acoustic lens 11 opposed to the sample is long, the ultrasonic beam spreads and does not become a plane wave, inevitably generating components of the vertical reflected wave. With the present invention, however, since an ultrasonic transducer of a large area can be constituted by using separated transmitting and receiving transducers or concave transducers, focused ultrasonic waves over a wide angle of incidence are generated and detected. Therefore, even if leaky elastic surface waves of various modes are superimposed, leaky elastic surface waves of all of them can be excited in the sample surface and detected.

Besides, information on the anisotropy of the elastic property of the surface of a material in a microscopic area therein can be reflected by the use of the point-focus ultrasonic beam. Accordingly, measurements from different directions of the sample will produce images of different contrasts and, further, measurements at different ultrasonic frequencies will provide images effective for analyzing the microscopic structure of the sample.

As described previously, it is preferable, for interference, that the pulse width of the high-frequency pulse from the high-frequency pulse generator be longer, but the pulse width is limited primarily for the necessity of signal separation from unnecessary echos and so forth. For this reason, in the event that the vertical reflected wave pulse and the leaky radiated wave pulse lag in time in arriving at the surface of the transducer according to the velocity of the elastic surface wave in the sample and the required interference effect cannot be produced, no measurement is possible with the prior art. With the present invention, however, an ultrasonic microscopic image or a curve corresponding to the V(z) curve can be obtained by shifting the signal phase or the time lag with a variable phase shifter.

Furthermore, the combined use of the variable phase shifter and a variable attenuator enables the application of, for example, an image comparison method, a convolution method and various other techniques developed so far in the field of image processing, thus permitting high precision measurements.

I claim:

1. A surface ultrasonic wave interference microscope comprising:
   a high-frequency pulse generator for generating high-frequency pulses produced by pulse modulating a carrier of an ultrasonic frequency;
   a transmitting ultrasonic transducer which is supplied with the high-frequency pulses from the high-frequency pulse generator and forms a transmitting focused ultrasonic beam for exciting a leaky elastic surface wave in the surface of a sample;
   a holder for holding the sample;
   a receiving ultrasonic transducer which receives the leaky elastic surface wave propagating in the sample surface and then reradiating therefrom and forms a receiving focused ultrasonic beam;
   a reference signal generating means for creating a reference signal from the carrier of the high-frequency pulses; and
   a mixing circuit for mixing the reference signal from the reference signal generating means and the received signal from the receiving ultrasonic transducer.

2. A surface ultrasonic wave interference microscope according to claim 1 wherein points of intersection of the center axes of the transmitting focused ultrasonic beam and the receiving focused ultrasonic beam with the surface of the sample are spaced apart from each other.

3. A surface ultrasonic wave interference microscope according to claim 2 further including a drive means for moving the sample holder and the transmitting and receiving ultrasonic transducers relative to each other.

4. A surface ultrasonic wave interference microscope according to claim 2 further including a relative phase shifting means whereby the phase difference between the reference signal and the received signal, which are supplied to the mixer, is varied relative to each other.

5. A surface ultrasonic wave interference microscope according to claim 4 further including a display which displays the mixer output corresponding to variations in the phase difference between the reference signal and the received signal, by plotting the value corresponding to the phase difference by the relative phase shifting means on one axis of the display screen and the intensity of the mixer output on an axis perpendicular to the said one axis.

6. A surface ultrasonic wave interference microscope according to claim 5 wherein the relative phase shifting means is a drive means whereby the sample holder and the transmitting and receiving ultrasonic transducers are moved relative to each other in a direction substantially perpendicular to the sample surface.

7. A surface ultrasonic wave interference microscope according to claim 5 wherein the relative phase shifting means is a drive means whereby one of the transmitting and receiving ultrasonic transducers and the sample holder are moved relative to each other in the direction of arrangement of points of intersection of the surface of the sample with the center axes of the both transducers.

8. A surface ultrasonic wave interference microscope according to claim 5 wherein the relative phase shifting means is a variable phase shifter for shifting the phase of the reference signal.

9. A surface ultrasonic wave interference microscope according to claim 5 wherein the relative phase shifting means is a variable phase shifter for shifting the phase of the received signal.

10. A surface ultrasonic wave interference microscope according to claim 5 wherein the relative phase shifting means is a variable phase shifter for shifting the phase of the carrier of the high-frequency pulses.

11. A surface ultrasonic wave interference microscope according to claim 5 wherein the relative phase shifting means is a frequency controlling means for changing the frequency of one of the carrier of the high-frequency pulses and the reference signal.

12. A surface ultrasonic wave interference microscope according to claim 6 wherein the focal points of the transmitting and receiving ultrasonic transducers are set at the same position.

13. A surface ultrasonic wave interference microscope according to any one of claims 7 to 11 wherein the focal points of the transmitting and receiving ultrasonic transducers are positioned substantially on the surface of the sample.

14. A surface ultrasonic wave interference microscope according to claim 6 or 7 further including a variable phase shifter which shifts the phase of one of the reference signal and the received signal in synchronism with the movement by the drive means, thereby maintaining a fixed phase difference between the reference signal and the received signal.

15. A surface ultrasonic wave interference microscope according to claim 14 further including a level regulator capable of changing the level of one of the reference signal and the received signal.

16. A surface ultrasonic wave interference microscope according to claim 15 wherein the drive means moves the transmitting and receiving ultrasonic transducers and the sample holder relative to each other in the direction perpendicular to the surface of the sample, and which further includes a compensating level regulator for changing the level of one of the reference signal and the received signal in synchronism with the movement by the drive means, thereby compensating for attenuation of the ultrasonic waves between the transmitting and receiving ultrasonic transducers and the sample surface which results from the movement by the drive means.

17. A surface ultrasonic wave interference microscope according to claim 3 wherein the drive means moves the sample holder and the transmitting and receiving ultrasonic transducers in parallel to the surface of the sample and scans the sample two-dimensionally, and which further includes a display for providing a two-dimensional display of the mixer output at each point on the sample surface during the two-dimensional scanning thereof.

18. A surface ultrasonic wave interference microscope according to claim 17 further including a rotating means for turning the sample holder and the transmitting and receiving ultrasonic transducers relative to each other in parallel to the surface of the sample.

19. A surface ultrasonic wave interference microscope according to claim 18 further including a variable phase shifter capable of adjusting the phase of one of the reference signal and the received signal which are provided to the mixer.

20. A surface ultrasonic wave interference microscope according to claim 18 further including a level regulator capable of regulating the level of one of the reference signal and the received signal which are provided to the mixer.

21. A surface ultrasonic wave interference microscope according to any one of claims 4, 6, 17, and 18 wherein the transmitting and receiving ultrasonic transducers are each a concave transducer having a transducer element mounted on a curved face of an acoustic lens and the acoustic lens of each transducer is formed by an ultrasonic medium common to the other transducer.

22. A surface ultrasonic wave interference microscope according to claim 21 which further includes sound absorbers, each mounted on the acoustic lens between the transducer elements of one of the transmitting and receiving ultrasonic transducers.

23. A surface ultrasonic wave interference microscope according to claim 22 wherein the curved face of the acoustic lens on which each transducer element is mounted is spherical and the face of the acoustic lens opposite the sample is also spherical so that the focused ultrasonic beams for transmission and reception are formed as point-focus ultrasonic beams; third and fourth transducer elements are mounted on the acoustic lens between the said transducer elements in a direction perpendicular to the direction of their arrangement, the third and fourth transducer elements and the acoustic lens constituting third and fourth point-focus ultrasonic transducers; the distance between points of intersection of the center axes of focused ultrasonic beams by the third and second point-focus ultrasonic transducers with the surface of the sample is made different from the distance between the points of intersections of the center axes of the transmission and reception focused ultrasonic beams with the surface of the sample; and a selective drive means is provided whereby the high-frequency pulses are supplied to at least one of the third and fourth point-focus ultrasonic transducers instead of to the transmitting ultrasonic transducer and the output of at least the other of the third and fourth point-focus ultrasonic transducers is supplied to the mixer instead of the output of the receiving ultrasonic transducer.

24. A surface ultrasonic wave interference microscope according to any one of claims 4, 6, 17 and 18 wherein the transmitting and receiving ultrasonic transducers form point-focus ultrasonic beams.

25. A surface ultrasonic wave interference microscope according to any one of claims 4, 6 and 17 wherein the transmitting and receiving ultrasonic transducers form line-focus ultrasonic beams.

26. A surface ultrasonic wave interference microscope according to any one of claims 4, 6, 17 and 18 wherein the both transducer elements of the transmitting and receiving ultrasonic transducers are interconnected and the connection point is connected to the output side of the high-frequency pulse generator and the input side of the mixer via a duplexer for separating the signal to be transmitted and the received signal from each other.

* * * * *